(12) United States Patent
Kim (10) Patent No.: US 9,775,993 B2
(45) Date of Patent: Oct. 3, 2017

(54) ELECTRICITY AND MICROCURRENT GENERATOR

(71) Applicant: Chun Gi Kim, Gyeongsangbuk-do (KR)

(72) Inventor: Chun Gi Kim, Gyeongsangbuk-do (KR)

( * ) Notice: Subject to any disclaimer, the term of this patent is extended or adjusted under 35 U.S.C. 154(b) by 44 days.

(21) Appl. No.: 14/901,892

(22) PCT Filed: May 13, 2014

(86) PCT No.: PCT/KR2014/004260
§ 371 (c)(1),
(2) Date: Dec. 29, 2015

(87) PCT Pub. No.: WO2015/005575
PCT Pub. Date: Jan. 15, 2015

(65) Prior Publication Data
US 2016/0346535 A1   Dec. 1, 2016

(30) Foreign Application Priority Data

Jul. 9, 2013   (KR) .......................... 10-2013-0080521

(51) Int. Cl.
*A61N 1/20*    (2006.01)
*A61N 1/04*    (2006.01)
*A61N 1/32*    (2006.01)
*A61N 1/378*   (2006.01)
*A61H 39/00*   (2006.01)
*A61N 1/34*    (2006.01)

(52) U.S. Cl.
CPC ........... *A61N 1/205* (2013.01); *A61H 39/002* (2013.01); *A61N 1/0456* (2013.01); *A61N 1/0468* (2013.01); *A61N 1/0492* (2013.01); *A61N 1/20* (2013.01); *A61N 1/326* (2013.01); *A61N 1/378* (2013.01); *A61H 2201/0138* (2013.01); *A61H 2201/10* (2013.01); *A61H 2201/1207* (2013.01); *A61H 2201/165* (2013.01); *A61N 2001/34* (2013.01)

(58) Field of Classification Search
CPC ...... A61N 1/3785; A61N 1/205; H01M 8/004
See application file for complete search history.

(56) References Cited

U.S. PATENT DOCUMENTS 2,622,166 A * 12/1952 Wallace ................. H01H 75/04
                                                   188/314
3,842,843 A * 10/1974 Mourot .................... A61N 1/02
                                                    429/406

FOREIGN PATENT DOCUMENTS

| JP | 05-056154 U | 7/1993 |
|---|---|---|
| JP | 2002-030504 A | 1/2002 |
| KR | 10-2008-0013468 A | 2/2008 |
| KR | 10-1031127 B1 | 4/2011 |
| KR | 20-2012-0001299 U | 2/2012 |
| KR | 20-2012-0008512 U | 12/2012 |

* cited by examiner

*Primary Examiner* — Michael Kahelin
(74) *Attorney, Agent, or Firm* — Novick, Kim & Lee, PLLC; Jae Youn Kim (57) ABSTRACT

The present invention relates to a microcurrent generator capable of generating microcurrents by utilizing a gap between different metals and obtaining a healing effect by using the generated microcurrents. The present invention relates to a configuration of generating microcurrents by forming a gap (G) between a first metal (10) and a second metal (20) made from different materials.

3 Claims, 8 Drawing Sheets

ELECTRICITY AND MICROCURRENT GENERATOR

TECHNICAL FIELD

The present invention relates to an electricity and microcurrent generator, and more specifically, to a generator for generating a microcurrent by utilizing a gap between different metals. This is a device which can be used in an electrical product and is helpful for healing a disease by creating and using the microcurrent as needed.

BACKGROUND ART

Generally, electricity is generated by using a generator, a motor or a battery having a recharging function.

Therefore, an apparatus for generating electricity is needed to generate electricity, and a predetermined energy is needed to drive the apparatus.

In addition, even when a treatment for a disease is provided using a current, a battery or electricity pulled in a building is utilized after being transformed into microelectricity.

Recently, the microcurrent is used to treat a neurological disorder or a brain disorder (depression, Parkinson's disease, epilepsy or the like).

A minute electric current (10 to 60 microamperes, −70 to 50 millivolts), which is referred to as a bioelectric current, flows in a human body. The bioelectric current is a life energy which triggers neural transmission and accomplishes all life activities in a human body, such as ATP synthesis, protein synthesis, DNA synthesis, exercise of internal organs, secretion of hormones, flow of body fluids and the like. Particularly, the bioelectric current functions as a medium for sharing genetic information (DNA) of each cell, and, to this end, a bioelectric current of a proper intensity is needed.

If the microcurrent (bioelectric current) of a human body is weakened, physical health is damaged, and the mental state will be unstable. It is known that the bioelectric current of a proper intensity actively helps metabolism and blood circulation, improves immunity, and is effective in cell regeneration, pain relief, edema treatment and acceleration of hormone secretion, ATP synthesis, protein synthesis, DNA synthesis and the like.

Accordingly, development of a microcurrent generator capable of generating a microcurrent is attempted recently in a variety of ways.

As one of conventional microcurrent generators, a microcurrent generator capable of transforming electricity supplied by a battery into a microcurrent has been disclosed. However, there is a structural inconvenience in that when a battery is used, an apparatus for transforming battery power into AC electricity is needed or an apparatus for generating appropriate hertz of frequency needs to be equipped in order to generate a microcurrent of an appropriate level.

On the contrary, since the microcurrent generator of the present invention generates DC electricity by itself, such a complex structure is not needed. That is, the microcurrent generator of the present invention can be utilized as a device for DC electricity treatment.

As another conventional microcurrent generator, a microcurrent generator using a piezoelectric element capable of generating a microcurrent in response to a pressure applied has been disclosed. However, there is a problem in that the manufacturing cost increases as the piezoelectric element of high price is used, and since the microcurrent is generated only when an external force is applied, the position of applying the microcurrent will be very restricted.

In addition, conventionally, a microcurrent generator of a simple structure capable of generating a microcurrent when a magnet moves with respect to a coil has been disclosed. However, when there is no movement in the surrounding area (or no external force), the existing microcurrent generator does not generate a microcurrent since movement of the magnet is stopped, and only when an external force is applied or a movement is generated in the surrounding area, the magnet moves, and the microcurrent is generated, and thus there is a problem in that it is difficult to generate a continuous microcurrent and the microcurrent is generated intermittently.

Accordingly, although some measures for microcurrent generators capable of simplifying the structure, reducing the manufacturing and maintenance cost and improving efficiency of generating a microcurrent are proposed recently as shown in Korean Patent Registration No. 10-0945145 (Feb. 24, 2010), they are not sufficient, and development of an efficient microcurrent generating apparatus is earnestly required.

DISCLOSURE OF INVENTION

Technical Problem

Therefore, the present invention has been made in view of the above problems, and it is an object of the present invention to provide a microcurrent generator capable of solving the disadvantages of the prior art and generating electricity and a microcurrent by itself by utilizing a gap between metals of different materials without using a battery or general electricity.

Another object of the present invention is to provide a microcurrent generator capable of obtaining a healing effect by utilizing a DC microcurrent generated by itself.

Another object of the present invention is to provide a microcurrent generator capable of improving efficiency of generating a microcurrent and semi-permanently generating the microcurrent.

Another object of the present invention is to provide a microcurrent generator capable of simplifying the structure and reducing manufacturing and maintenance cost.

Technical Solution

To accomplish the above objects, the present invention provides a microcurrent generator which forms a gap between a first metal and a second metal of different materials and generates a current by using a diaphragm which can maintain the gap.

In addition, according to the present invention, one or more insertion holes are formed in the first metal, and the second metal is inserted in the insertion hole of the first metal to form a gap, and, in addition, a diaphragm for maintaining the gap is arranged in the gap, and terminals are connected to the first and second metals so that electricity can be supplied to an electrical product.

In addition, according to the present invention, terminal holes for inserting the terminals are formed in the first and second metals, respectively.

In addition, according to the present invention, the insertions hole of the first metal, the second metal and the terminal are formed in plurality to correspond to each other.

In addition, according to the present invention, third and fourth metals different from each other are sequentially arranged outside the first metal, and terminals corresponding to each other are provided in the first metal and the third and fourth metals.

In addition, according to the present invention, the first and second metals are formed of copper and zinc or iron and zinc.

In addition, according to the present invention, the gap between the first metal and the second metal is maintained to be 0.001 to 0.5 mm.

Advantageous Effects

According to the microcurrent generator of the present invention, there is an effect of generating a needed current by itself by forming a gap between a first metal and a second metal of different materials and supplying the microcurrent to an electrical product through a terminal, without using a battery or general electricity.

In addition, the present invention has an effect of obtaining various healing effects by generating a microcurrent by itself and using the microcurrent, structurally improving efficiency of generating the microcurrent, and semi-permanently generating the microcurrent.

In addition, the present invention may simplify the structure, reduce manufacturing and maintenance cost, consistently maintain the effect of the current or the microcurrent, and perform an intended healing function by stimulating acupuncture points, meridian points or affected areas through a terminal.

This is using metals of different electrical characteristics and has an effect of relieving blockage of electrical flow in a human body and healing pains and diseases generated by the blockage of electrical flow.

BEST MODE FOR CARRYING OUT THE INVENTION

Hereafter, the technical configuration of the present invention will be described in detail with reference to the accompanying drawings.

A microcurrent generator of the present invention is configured to generate a microcurrent by forming a gap G between a first metal 10 and a second metal 20 of different materials as shown in FIGS. 1 to 9.

Generally, electricity (current) refers to a phenomenon of flowing a current along a conducting wire, and the current flows from high potential to low potential within a conductor, and its direction is the direction of flowing positive electricity. The unit of the current is ampere (A).

In regards to the current generated like this, a current of one milliampere or less is referred to as a microcurrent, and a current over one milliampere is referred to as a general current.

Here, according to the electricity and microcurrent generator of the present invention, a general current over one milliampere and a microcurrent of one milliampere or less are generated according to the potential of the gap G and the material of a diaphragm between the first metal 10 and the second metal 20.

At this point, different metals having a large potential difference are preferably used as the first metal 10 and the second metal 20 to obtain a high current.

The present invention configured as described above may generate a current or a microcurrent of a different capacity according to the material of the diaphragm maintaining the gap and may generate electricity of a further larger capacity if a plurality of generators are connected in series or parallel.

Figure 1:
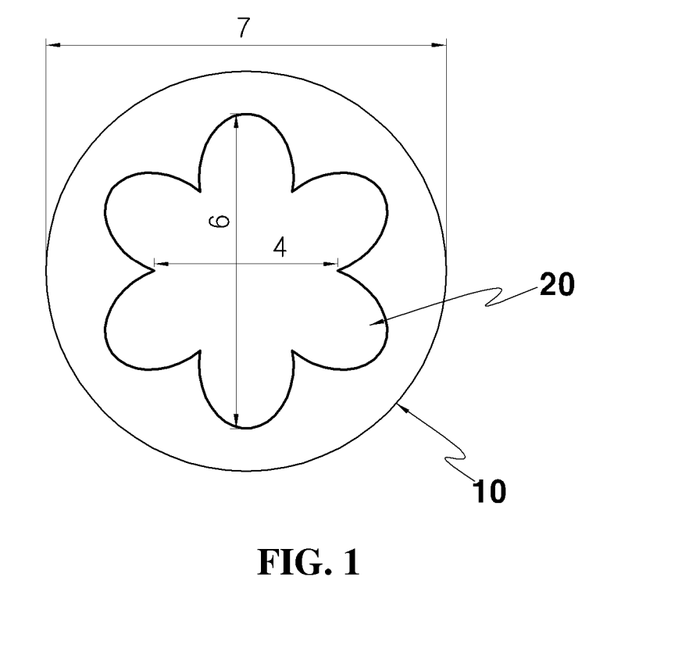
FIGS. 1, 2 and 3 are exemplary views showing examples of the present invention.
Figure 2:
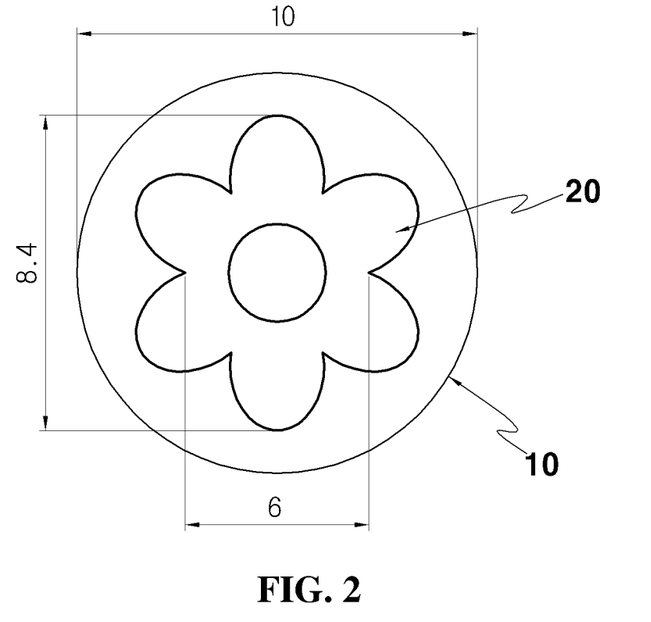
Figure 3:
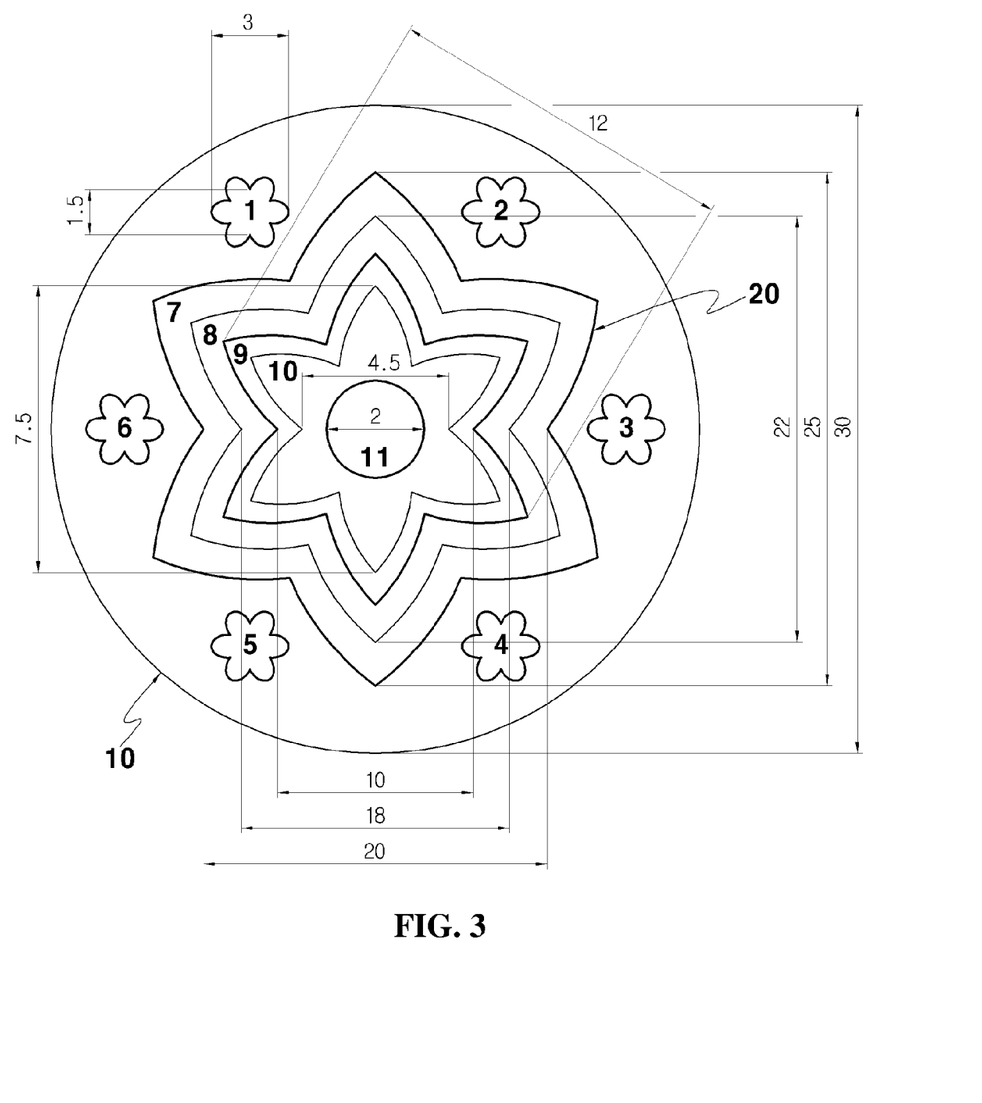
Figure 4:
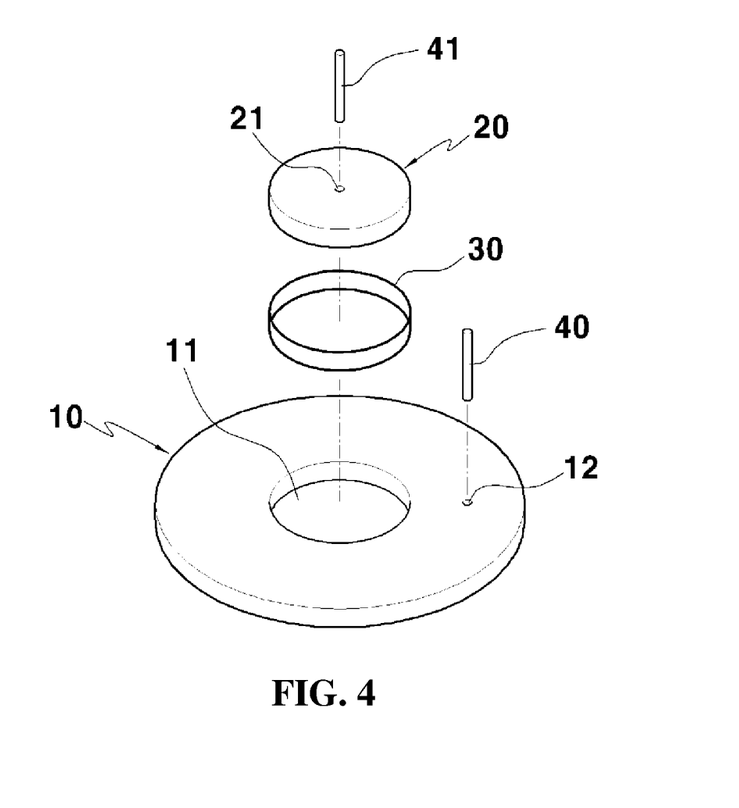
FIG. 4 is an exploded perspective view of the present invention.
Figure 5:
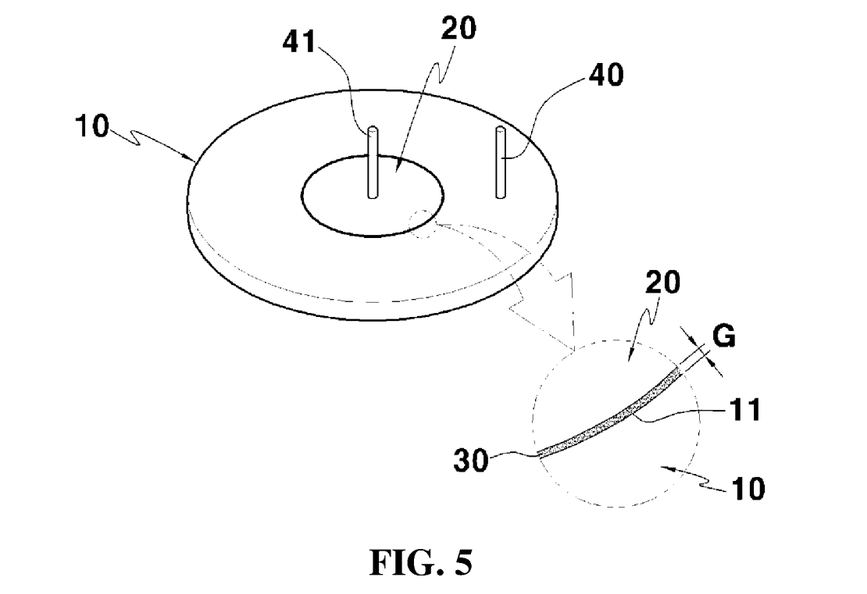
FIG. 5 is a perspective view of the present invention.
Figure 6:
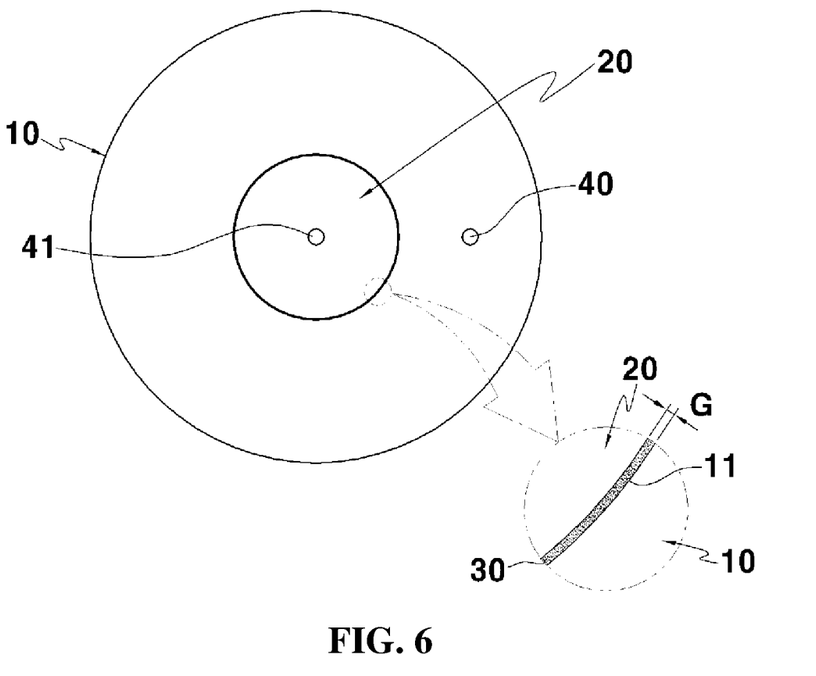
FIG. 6 is a plan view of the present invention.
Figure 7:
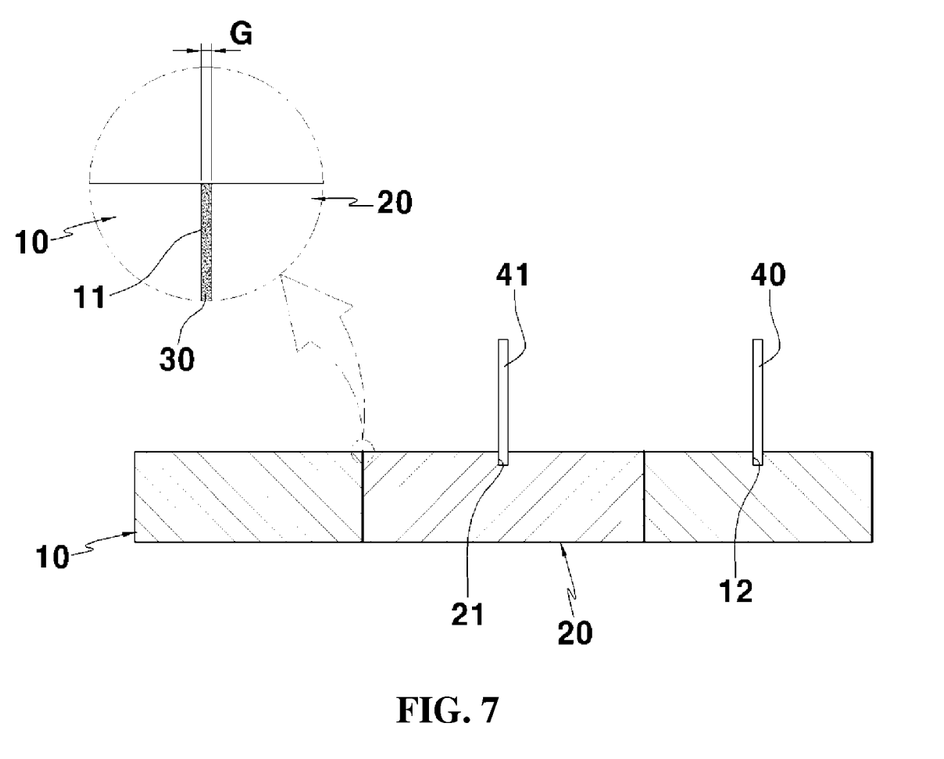
FIG. 7 is a cross-sectional view of the present invention.

In the present invention, as shown in FIGS. 1 to 3, an experiment has been carried out using three kinds of generators of different sizes and four kinds of diaphragms of different materials. The sizes of the electricity and microcurrent generators used in this experiment are as described below. The specifications of the different current generators are as described below.

FIG. 1—A generator having a diameter of 7 cm. The diameter of the first metal 10 is 7 cm, and the second metal 20 is a structure of a petal shape having a small diameter of 4 cm and a large diameter of 6 cm.

FIG. 2—A generator having a diameter of 10 cm. The diameter of the first metal 10 is 10 cm, and the second metal 20 is a structure of a petal shape having a small diameter of 6 cm and a large diameter of 8.4 cm.

FIG. 3—A generator having a diameter of 30 cm. The diameter of the first metal 10 is 30 cm, and No. 1 to No. 6 of the second metal 20 have a small diameter of 1.5 cm and a large diameter of 3 cm.

No. 7 of the second metal 20 has a small diameter of 20 cm and a large diameter of 25 cm.

No. 8 of the second metal 20 has a small diameter of 18 cm and a large diameter of 22 cm.

No. 9 of the second metal 20 has a small diameter of 10 cm and a large diameter of 12 cm.

No. 10 of the second metal 20 has a small diameter of 4.5 cm and a large diameter of 7.5 cm.

No. 11 of the second metal 20 has a diameter of 2 cm.

The materials and sizes of the diaphragm are as described below.

If the material of the diaphragm is paper, its thickness is 0.1 mm, width is 2 mm, and height is 15 mm.

If the material of the diaphragm is vinyl, its thickness is 0.2 mm, width is 2 mm, and height is 15 mm.

If the material of the diaphragm is a paper material containing 80% of moisture, its thickness is 0.3 mm, width is 2 mm, and height is 15 mm.

If the material of the diaphragm is a paper soaked in purified water, its thickness is 0.3 mm, width is a product of a large diameter of each second metal and 3.14, and height is 15 mm.

In the generator having a diameter of 7 cm, zinc is used as the material of the first metal 10, and red copper is used as the material of the second metal 20. When diaphragms of a 0.1 mm paper or 0.2 mm vinyl material arranged at intervals of 12 mm are used, a voltage of 127 mV to 285 mV and a current of 10 microamperes or less are generated.

In the generator having a diameter of 7 cm, zinc is used as the material of the first metal 10, and red copper is used as the material of the second metal 20. When a diaphragm of a paper material containing 80% of moisture is utilized, a voltage of 475 mV to 512 mV and a current of 360 microamperes are generated.

In the generator having a diameter of 7 cm, zinc is used as the material of the first metal 10, and red copper is used as the material of the second metal 20. When a paper soaked in purified water is utilized as a diaphragm, a voltage of 750 mV to 950 mV and a current of 2.20 amperes are generated.

In the generator having a diameter of 10 cm, zinc is used as the material of the first metal 10, and red copper is used as the material of the second metal 20. When a diaphragm of a 0.1 mm paper or 0.2 mm vinyl material is used, a voltage of 135 mV to 348 mV and a current of 10 microamperes or less are generated.

In the generator having a diameter of 10 cm, zinc is used as the material of the first metal 10, and red copper is used as the material of the second metal 20. When a diaphragm of a paper material containing 80% of moisture is utilized, a voltage of 432 mV to 579 mV and a current of 400 microamperes are generated.

In the generator having a diameter of 10 cm, zinc is used as the material of the first metal 10, and red copper is used as the material of the second metal 20. When a paper soaked in purified water is utilized as a diaphragm, a voltage of 850 mV to 950 mV and a current of 2.46 amperes are generated.

In the generator having a diameter of 30 cm, the structure of the first metal 10 and the second metal 20 is configured as a multi-layer structure as shown in the figure. Specifically, a multi-layer of eleven layers is formed, and the current between the first metal 10 and the second metal 20 is measured respectively according to the materials of the diaphragm.

The material of the first metal 10 is red copper, and zinc is used as the material of No. 1 to 7 of the second metal, red copper is used for No. 8 of the second metal, zinc is used for No. 9 of the second metal, red copper is used for No. 10 of the second metal, and zinc is used for No. 11 of the second metal. (see the figure for the sizes of No. 1 to 11 of the second metal) At this point, the sizes of No. 1 to No. 6 of the second metal are the same.

At this point, when a diaphragm of a 0.1 mm paper or 0.2 mm vinyl material is used, a voltage of 256 mV to 350 mV and a current of 10 microamperes or less are generated from No. 1 to No. 6 of the second metal.

When a diaphragm of a 0.1 mm paper or 0.2 mm vinyl material is used between No. 7 of the second metal 20 and the first metal 10, a voltage of 261 mV to 382 mV and a current of 10 microamperes or less are generated.

When a diaphragm of a 0.1 mm paper or 0.2 mm vinyl material is used between the zinc of No. 7 of the second metal 20 and the red copper of No. 8 of the second metal 20, a voltage of 258 mV to 360 mV and a current of 10 microamperes or less are generated.

When a diaphragm of a 0.1 mm paper or 0.2 mm vinyl material is used between the red copper of No. 8 of the second metal 20 and the zinc of No. 9 of the second metal 20, a voltage of 254 mV to 356 mV and a current of 10 microamperes or less are generated.

When a diaphragm of a 0.1 mm paper or 0.2 mm vinyl material is used between the zinc of No. 9 of the second metal 20 and the red copper of No. 10 of the second metal 20, a voltage of 265 mV to 347 mV and a current of 10 microamperes or less are generated.

When a diaphragm of a 0.1 mm paper or 0.2 mm vinyl material is used between the red copper of No. 10 of the second metal 20 and the zinc of No. 11 of the second metal 20, a voltage of 132 mV to 186 mV and a current of 10 microamperes or less are generated.

When a diaphragm of a paper material containing 80% of moisture is used in the generator having a diameter of 30 cm, a voltage of 410mV to 580mV and a current of 250 to 320 microamperes are generated from No. 1 to No. 6.

When a diaphragm of a paper material containing 80% of moisture is used between No. 7 of the second metal 20 and the first metal 10, a voltage of 500 mV to 550 mV and a current of 380 to 520 microamperes are generated.

When a diaphragm of a paper material containing 80% of moisture is used between the zinc of No. 7 of the second metal 20 and the red copper of No. 8 of the second metal 20, a voltage of 480 mV to 530 mV and a current of 360 to 430 microamperes are generated.

When a diaphragm of a paper material containing 80% of moisture is used between the red copper of No. 8 of the second metal 20 and the zinc of No. 9 of the second metal 20, a voltage of 480 mV to 530 mV and a current of 420 to 550 microamperes are generated.

When a diaphragm of a paper material containing 80% of moisture is used between the zinc of No. 9 of the second metal 20 and the red copper of No. 10 of the second metal 20, a voltage of 380 mV to 450 mV and a current of 420 to 500 microamperes are generated.

When a diaphragm of a paper material containing 80% of moisture is used between the red copper of No. 10 of the second metal 20 and the zinc of No. 11 of the second metal 20, a voltage of 380 mV to 420 mV and a current of 720 to 800 microamperes are generated.

When a paper soaked in purified water is used as a diaphragm in the generator having a diameter of 30 cm, a voltage of 750 mV to 800 mV and a current of 2.2 milliamperes are generated from No. 1 to No. 6 of the second metal.

When a paper soaked in purified water is used as a diaphragm between No. 7 of the second metal 20 and the first metal 10, a voltage of 850 mV to 980 mV and a current of 2.5 milliamperes are generated.

When a paper soaked in purified water is used as a diaphragm between the zinc of No. 7 of the second metal 20 and the red copper of No. 8 of the second metal 20, a voltage of 750 mV to 850 mV and a current of 2.24 milliamperes are generated.

When a paper soaked in purified water is used as a diaphragm between the red copper of No. 8 of the second metal 20 and the zinc of No. 9 of the second metal 20, a voltage of 750 mV to 850 mV and a current of 2.2 milliamperes are generated.

When a paper soaked in purified water is used as a diaphragm between the zinc of No. 9 of the second metal 20 and the red copper of No. 10 of the second metal 20, a voltage of 680 mV to 750 mV and a current of 2.2 milliamperes are generated.

When a paper soaked in purified water is used as a diaphragm between the red copper of No. 10 of the second metal 20 and the zinc of No. 11 of the second metal 20, a voltage of 980 mV to 1.3V and a current of 2.54 milliamperes are generated.

When the microcurrent is used for treatment, microcurrents of different microamperes are used according to symptoms. For example, a microcurrent used for regeneration of bones is between 10 to 60 microamperes. A microcurrent used for ATP synthesis, DNA synthesis, protein synthesis and pain relief is 400 microamperes. A microcurrent used for virus suppression is between 20 to 60 microamperes.

Since the microcurrent generator of the present invention may generate microcurrents of various intensities according to the material of the diaphragm, it can be applied to a wide range of disease symptoms.

Examples of healthcare equipment using the microcurrent of the present invention are described below.

The microcurrent generated in the gap G between the first metal 10 and the second metal 20 can be used for the good influence to a human body or for the treatment purpose by contacting the microcurrent generator to a specific acupuncture or meridian point or other portions of a body. The effects of using the microcurrent can be confirmed in the papers listed below. 1) Hye-Jin Oh, Jung-Woo Kim, et al., "The effect of Microcurrent Stimulation on Histological Structure of Wound in Rat", The Journal of Korean Society of Physical Therapy, Korean Society of Physical Therapy, 2008, 2) Hyen-ju Oh, Jong-youl Kim, et al., "The Effects of Microcurrent Stimulation on Recovery of Function and Pain in Chronic Low Back Pain", The Journal of the Korean Society of Physical Medicine vol. 3 no. 1, February 2008, 3) Rae-Joon Park, Sang-Joon Choi, et al., "Effects of Induced Microcurrent Shoes on Fatigue and Pain in Painful Foot to Patients with Plantar Fascitis", The Journal of Korean Society of Physical Therapy vol. 18 no. 1, February 2006, 4) Yoon-Mi Lee, Rae-Joon Park, et al., "Effects of Induced Microcurrent Shoes on Change of Blood Circulation to patients with Chronic Plantar Fascitis", The Journal of Korean Society of Physical Therapy vol. 18 no. 3, June 2006, and 5) Young-Han Park, "The Effect of Electrical Stimulation on Bacterial Growth", The Journal of Korean Society of Physical Therapy vol. 6 no. 1, 1994.

Other than these, several papers showing that cancer cells can be dedifferentiated through a microcurrent have been published. Steven Smith observed in vitro experiments that growing malignant lymphoma cells can be transformed into positive cellulose.

In the 1950s, C. E. Humphrey and E. H. Seal of Johns Hopkins University observed that growth of cancer cells of a rat can be stopped if pulsed DC electricity is applied, and L. Norton and L. Tansman of Mount Sinai School of Medicine in New York City and W. Riegelson of Virginia School of Medicine reported that progress of cancer is suppressed if pulsed electromagnetic fields are radiated on cancer cells of a rat. In the 1960s, Kenneth MacLean insisted that cancer can be cured if magnetic fields are used for the cancer of a rat. Robert Becker, who is a Novel Prize winner and the author of the book 'The Body Electric', has discovered that if a microcurrent is applied to cancer cells, the cancer cells can be dedifferentiated to normal cells.

In the report of a study published by Ngok Cheng in 1987, microcurrents increase an energy ATP generation rate in a cell by 500% and increases a protein production rate and a waste material removal function by 70%.

The effect of microcurrents on the generation of bones and healing of wounds has been proved by English Academics Professor Tim Watson of Hertfordshire University in England, who is one of world's great scholars The microcurrent is effective on mitigation of spinal nerve irritability of a spastic patient Professor Toshiaki Suzuki of Kansai University, Japan A result of animal experiment showing that microcurrent stimulation is helpful for fracture healing and bone union Professor Mi-Suk Cho of Korea Nazarene University Reported antibacterial effects through silver nano coated electrode Medical device clinical trial center team of Yeungnam University Delay decrease of growth hormone, Positive effect on increase of growth hormone Doctor In-Bum Suh of College of Medicine of Kangwon National University Microcurrent and high voltage pulsed galvanic current stimulation are effective on fibular fracture healing of rabbits Seung-Hyun Ko, Bum-Chul Yoon, Ji-Sung Kim, Kyung-Ok Min A study on the effect of microcurrent therapy on rheumatoid arthritis induced white rat Hyun-Min Lee, Yun-Won Chae Observing the effects of the microcurrent therapy from the biochemical aspect, the microcurrent increases ATP by 500%, accelerates protein synthesis, and increases permeability of the cell membrane by 40%. In addition, the microcurrent accelerates DNA synthesis and T lymphocyte activities.

Accordingly, such a microcurrent generator of the present invention can be used for making a bed, a desk, a carpet, an accessory, a bracelet, a necklace, healthcare equipment or the like, and, other than these, it can be manufactured and used as an interior fixture of a building or various healing products.

In addition, the microcurrent generator of the present invention can be used in an electronic device in which a microcurrent is used.

Hereinafter, various embodiments of the present invention will be described in detail with reference to the accompanying drawings.

According to an embodiment of the present invention, as shown in FIGS. 4 to 7, an insertion hole 11 is formed in the first metal 10, and the second metal 20 is inserted in the insertion hole 11 to form a gap G, and a diaphragm 30 for maintaining the gap is arranged in the gap G, and terminals 40 and 41 having a positive electrode (+) and a negative electrode (−) are connected to the first and second metals 10 and 20, respectively. At this point, although the first metal 10, the insertion hole 11 and the second metal 20 are preferably formed in a circular shape as shown in the figures, it is clearly stated that they can be formed in a variety of shapes as needed.

In addition, terminal holes 12 and 21 for inserting the terminals 40 and 41 are formed in the first and second metals 10 and 20, respectively. At this point, if the terminal holes 12 and 21 are used, the terminals 40 and 41 can be easily connected to the first and second metals 10 and 20.

Figure 8:
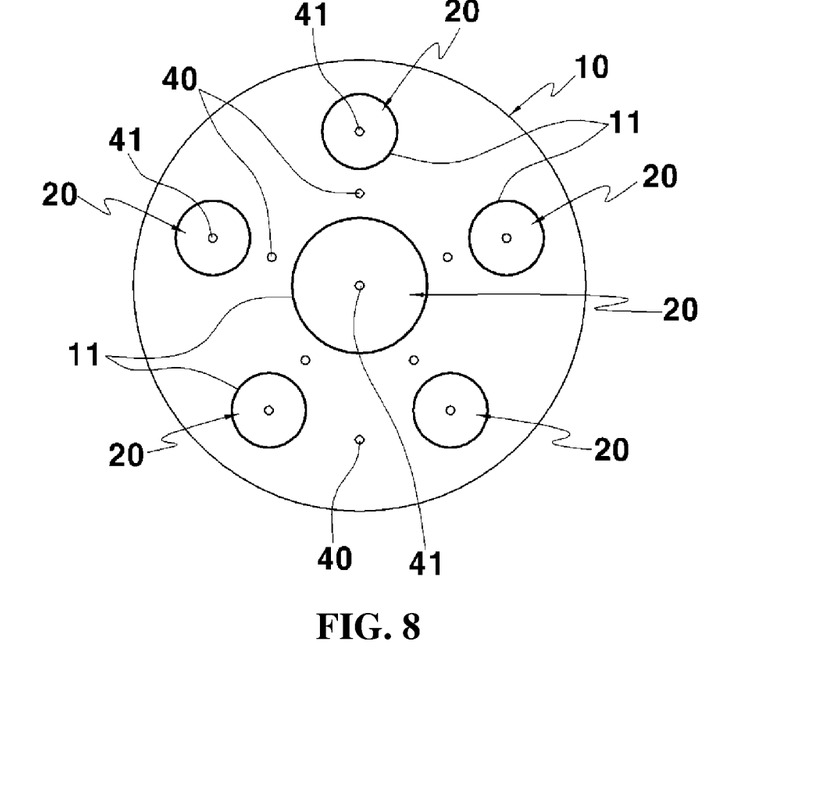
FIG. 8 is a plan view showing another embodiment of the present invention.

According to another embodiment of the present invention, as shown in FIG. 8, the insertion holes 11, the second metals 20 and the terminals 40 and 41 are formed in plurality corresponding to each other. At this point, a gap and a diaphragm are also formed between each of the insertion holes 11 and each of the second metals 20 respectively as described above. Accordingly, a microcurrent is generated in the gaps of the plurality of second metals 20.

Figure 9:
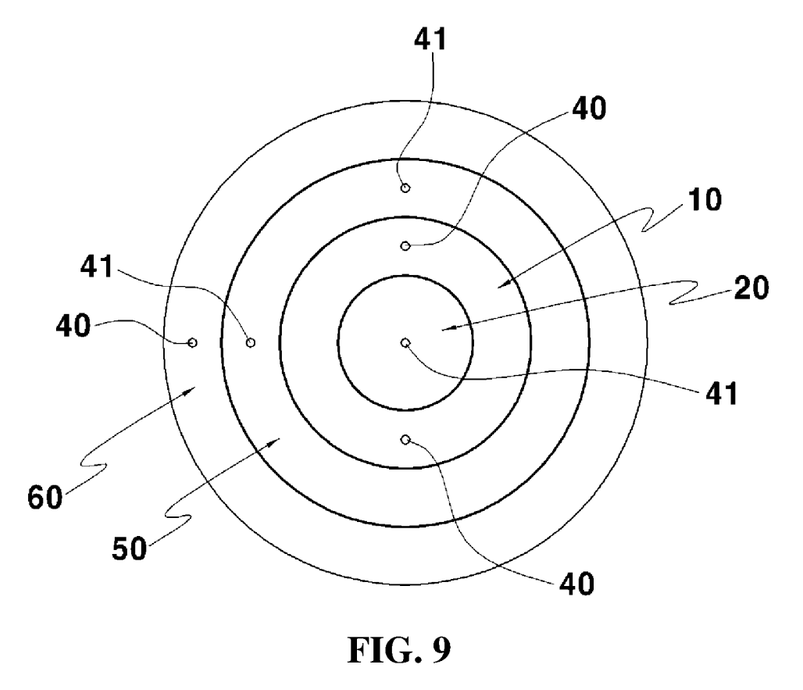
FIG. 9 is a plan view showing still another embodiment of the present invention.

According to still another embodiment of the present invention, as shown in FIG. 9, third and fourth metals 50 and 60 different from each other are sequentially arranged outside the first metal 10, and terminals 40 and 41 corresponding to each other are provided in the first metal 10 and the third and fourth metals 50 and 60. At this point, a gap and a diaphragm are also formed between the first, third and fourth metals 10, 50 and 60 respectively as described above. Accordingly, a microcurrent is generated in the gap between the third and fourth metals 50 and 60.

It is preferable that a metal of a material the same as that of the second metal 20 is arranged as the third metal 50, and a metal of a material the same as that of the first metal 10 is arranged as the fourth metal 60.

On the other hand, it is clearly stated that fifth, sixth and other metals can be sequentially arranged outside the fourth metal 60, and, in addition, it may be configured to generate a microcurrent by forming a plurality of insertion holes in the first, third and fourth metals 10, 50 and 60 as shown in FIG. 8.

According to an embodiment of the present invention, the first and second metals 10 and 20 are formed of copper and zinc or iron and zinc. At this point, although the first and second metals 10 and 20 are preferably formed of copper and zinc or iron and zinc, a material having superior electrical characteristics such as gold, silver, aluminum or stainless steel can be used as needed, and it is clearly stated that any other material can be used if it has high electrical conductivity although it is not one of the metals described above.

According to an embodiment of the present invention, the gap G is preferably maintained to be 0.001 to 0.5 mm.

The microcurrent generator of the present invention configured as described above is advantageous in that the generator may generate a microcurrent by itself by utilizing a gap of metals of different materials without using a battery or general electricity and has an advantage of obtaining a healing effect using the microcurrent generated by itself.

In addition, the microcurrent generator of the present invention has an advantage of improving efficiency of generating a microcurrent and semi-permanently generating the microcurrent.

In addition, the microcurrent generator of the present invention has an advantage of simplifying the structure and reducing manufacturing and maintenance cost.

In addition, the microcurrent generator of the present invention can be used in place of an electricity generator used at home, as well as for generating a microcurrent.

That is, as described above, the third and fourth metals 50 and 60 different from each other are arranged outside the first metal 10, and terminals 40 and 41 corresponding to each other are provided in the first metal 10 and the third and fourth metals 50 and 60. At this point, an electricity generator is configured as a gap and a diaphragm are also formed between the first, third and fourth metals 10, 50 and 60 respectively.

If the electricity generator configured as described above is configured in plurality and created as a unit in a box, needed electricity can be produced. Accordingly, when a large capacity of electricity is desired to be produced, the needed electricity can be produced if a plurality of the electricity generator units is provided, and the electricity generators created as a unit can be connected in series or parallel to obtain a current and a voltage as needed.

The electricity generator of the present invention configured as described above has an advantage of low installation and management cost compared with existing solar heat electricity, and since energy consumed for driving the generator is not used unlike a generator or a motor, it can be provided as a green energy.

INDUSTRIAL APPLICABILITY

The microcurrent generator of the present invention generates a needed current by itself and can be used for healing pains and diseases by stimulating acupuncture points, meridian points or affected areas through a terminal.

The microcurrent generator of the present invention can be used for making a bed, a desk, a carpet, an accessory, a bracelet, a necklace, healthcare equipment or the like, and, other than these, it can be manufactured and used as an interior fixture of a building or various healing products.

In addition, the microcurrent generator of the present invention can be used in an electronic device in which a microcurrent is used.

The invention claimed is:

1. A generator for generating a current, comprising:
a diaphragm arranged in a gap between a first metal and a second metal of different materials,
wherein a diameter of the first metal is 7 to 30 cm, the gap is maintained to be 0.001 to 0.5 mm, the diaphragm is formed of paper or vinyl, the first metal includes a first terminal hole for inserting a first terminal, the second metal includes a second terminal hole for inserting a second terminal, and the first and second terminals are connected to the first and second metals, respectively to supply the current to an electrical product.

2. The generator according to claim 1, wherein the first metal includes an insertion hole to receive the second metal.

3. The generator according to claim 1, further comprising a third and a fourth metals sequentially arranged outside the first metal, and a third and a fourth terminals provided in the third and fourth metals, respectively.

* * * * *